(12) United States Patent
Alt

(10) Patent No.: US 6,829,503 B2
(45) Date of Patent: Dec. 7, 2004

(54) CONGESTIVE HEART FAILURE MONITOR

(75) Inventor: Eckhard Alt, Ottobrunn (DE)

(73) Assignee: SciCoTec GmbH, Gruenwald (DE)

( * ) Notice: Subject to any disclaimer, the term of this patent is extended or adjusted under 35 U.S.C. 154(b) by 98 days.

(21) Appl. No.: 10/155,771

(22) Filed: May 25, 2002

(65) Prior Publication Data

US 2003/0220580 A1 Nov. 27, 2003

(30) Foreign Application Priority Data

Oct. 1, 2001 (DE) .......................... 101 48 440

(51) Int. Cl.⁷ ................................. A61B 5/05
(52) U.S. Cl. ..................................... 600/547
(58) Field of Search ........................ 600/547, 508, 600/485, 300, 510, 481, 301; 607/9; 128/903, 904

(56) References Cited

U.S. PATENT DOCUMENTS

| 4,899,758 | A | * | 2/1990 | Finkelstein et al. | ......... 600/485 |
|---|---|---|---|---|---|
| 5,876,353 | A | | 3/1999 | Riff | |
| 5,957,861 | A | | 9/1999 | Combs et al. | |
| 6,104,949 | A | * | 8/2000 | Pitts Crick et al. | ......... 600/547 |
| 6,336,903 | B1 | * | 1/2002 | Bardy | ......... 600/508 |
| 6,351,667 | B1 | * | 2/2002 | Godie | ......... 600/547 |
| 6,416,471 | B1 | * | 7/2002 | Kumar et al. | ......... 600/300 |
| 6,512,949 | B1 | | 1/2003 | Combs et al. | |
| 2002/0115939 | A1 | * | 8/2002 | Mulligan et al. | ......... 600/510 |

* cited by examiner

Primary Examiner—Charles Marmor
Assistant Examiner—Brian Szmal

(57) ABSTRACT

A device-implemented method is disclosed for early detection and monitoring of congestive heart failure in a patient. Ongoing measurements of impedance of a portion of the patient's body generally occupied by the lungs are performed by an implanted device, and, when the impedance measurements are determined by internal circuit components of the device to exceed a predetermined threshold value indicative of a need for immediate attention to a condition of congestive heart failure, a patient and/or physician alert is emitted by the device. An implant site at the left lower anterior lateral hemithorax is preferred.

32 Claims, 4 Drawing Sheets

CONGESTIVE HEART FAILURE MONITOR

BACKGROUND OF THE INVENTION

The present invention relates generally to implantable medical devices, and more particularly to an implantable device for detecting and monitoring the progression of congestive heart failure.

Many patients who have suffered one or more myocardial infarctions subsequently require treatment for congestive heart failure (CHF). The left heart fails while the pumping function of the right heart remains adequate, because the latter has only about 20% of the workload of the former. This leads to an increase in blood volume congested to the lungs, resulting in pulmonary congestion, build up of edema, and congestion of internal organs including the stomach and intestines. Increased fluid in the stomach and intestines reduce their ability to absorb drugs prescribed for treatment of CHF, particularly diuretics. The congestion is often accompanied by a worsening of myocardial function, with consequent drop in blood pressure and reduced renal perfusion, which only further aggravates the congestive situation. Thus, late recognition of congestion leads to increased dosages of oral diuretics that are unsuccessful to treat the condition, ultimately requiring that the patient be hospitalized.

Avoidance of hospitalization and the pitfalls of late treatment require detection of CHF at an early stage, so that the prescribed drugs can be fully absorbed and effective. If detected early, a combination of diuretics and other drugs can slow the progress of the disease and allow the patient to enjoy an improved lifestyle.

It is a principal aim of the present invention to provide an implantable heart failure monitor which is capable of achieving very early detection of CHF.

SUMMARY OF THE INVENTION

The implantable medical device of the present invention is of size smaller than a typical pacemaker device—about the size of a thumb. It is implanted in a subcutaneous pocket formed by the surgeon in the patient's chest, under local anesthesia and minimally invasive requirements. The device includes a hermetically sealed can with appropriate electronic circuitry inside. A set of can-mounted electrodes is used to measure the impedance of the adjacent tissue and most especially the lung tissue. The progressive retention of fluid in the lungs and congestion of the ventricle together result in a reduced impedance measurement that is monitored either continuously or periodically by the device.

In a preferred mode of operation, the device alerts the patient and the attending physician when a diagnostic threshold is reached which is indicative of the progression of CHF. The overall architecture of the device follows implantables practice, and is a stand-alone monitoring device. However, it should be appreciated that the partitioning of the device is flexible and the division of sensing and analysis structures can be shared between implanted and external (remote, i.e., non-implanted) devices. Conventional programming and telemetry links can be used to connect the implanted device to the remote device.

For example, the signal processing may be performed entirely internally within the device, or the device may operate as a data logger and communicate with an external programmer device which participates in data reduction and analysis.

Although specific structures are shown as being dedicated to specific tasks, it should be apparent that certain functions may be shared if the device is integrated with other diagnostic or therapeutic devices. For example, the electrode set used to determine the impedance of the lungs could be used for additional purposes.

BRIEF DESCRIPTION OF THE DRAWINGS

The above and other aims, objectives, aspects, features and attendant advantages of the invention will be further understood from a reading of the following detailed description of the best mode presently contemplated for practicing the invention, taken with reference to certain presently preferred implementations and methods, and in conjunction with the accompanying drawings, in which.

Figure 1:
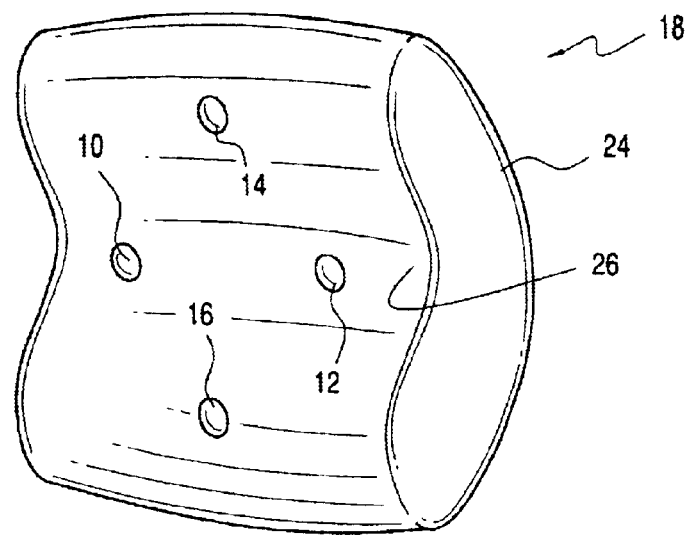
FIG. 1 is an exterior view of an embodiment of the device.

DETAILED DESCRIPTION OF THE PRESENTLY CONTEMPLATED BEST MODE OF PRACTICING THE INVENTION

The device of the invention is disclosed in the preferred implementation as being a stand-alone diagnostic device to simplify the description of its operation. Throughout the several views of the drawings identical reference numerals indicate identical structure. Views of the device either alone or as implanted are not intended to represent actual or relative sizes.

FIG. 1 illustrates the exterior of the device 18 in its presently preferred embodiment. Device 18 includes a circuit module (to be discussed below in conjunction with the description of FIG. 3) within a hermetically sealed "can" or case 24 composed, for example, of titanium. The size of the case 24 is clearly dictated by the size of the internal circuit components and wiring included printed circuit board(s) and other forms, but preferably is very small, currently about 5.0 cm long by 2.0 cm wide by less than 1.0 cm thick.

Case 24 has a curvilinear shape which presents a concave shape or surface 26 on one side (in contrast to an edge of the case) and a convex shape on the opposite side of the case. Four surface mounted electrodes 10, 12, 14 and 16 are positioned in spaced-apart relationship on the slightly concave surface 26, with each electrode being electrically insulated from the case 24 itself. The electrodes should be of low polarization, preferably composed of or coated with iridium oxide. By way of example, "inner" electrodes 10 and 12 are spaced apart on the concave side inward of opposite edges and centrally along the length of the case, while "outer" electrodes 14 and 16 are spaced further apart—preferably, by at least about 4 cm—on that same side inward of opposite edges and centrally along the width of the case. The shape of the case is designed (and preferred) to conform to the shape of the anatomy of the human chest. With the concave side of the case placed toward the interior of the body within the implant site of device 18, the device is prevented from turning within its subcutaneous pocket which would otherwise position the surface electrodes at the wrong side—namely, toward the exterior of the patient's body. The reason for this positioning will become apparent as the description proceeds.

Figure 2:
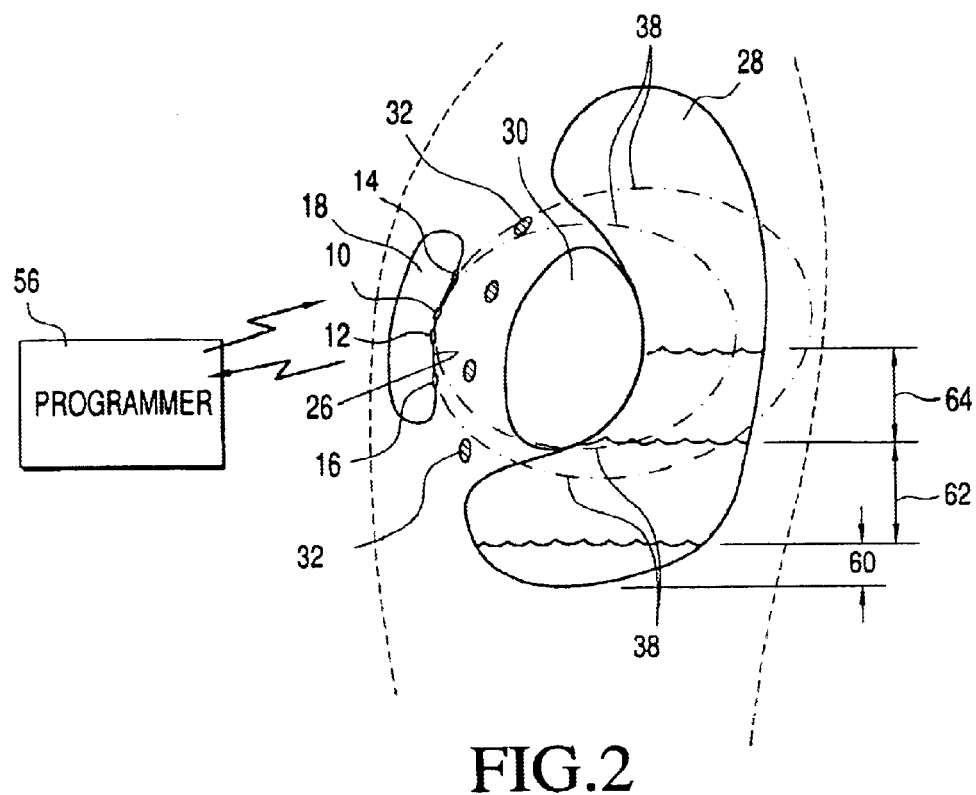
FIG. 2 is a schematic representation of an implantation of the device in the body of a patient.

The most preferred implant site of the device is the left lower anterior lateral hemithorax of the patient's body as shown in FIG. 2. In part, this is because optimal sensing occurs with the device placed slightly to the left of the patient's midline. FIG. 2 illustrates in schematic form a side view of a patient (in phantom) with the device 18 implanted in a pectoral of the chest over the basal region of lungs 28 and heart 30, outside the rib cage 32. An implantation at the preferred site places the device on the left anterior thorax side between the 5th and 6th intercostals space. In this position of the device, an impedance signal is developed which represents the impedance of the lungs and heart tissue by virtue of current injected into the circuit path that establishes a field through that portion of the body from device 18.

Figure 3:
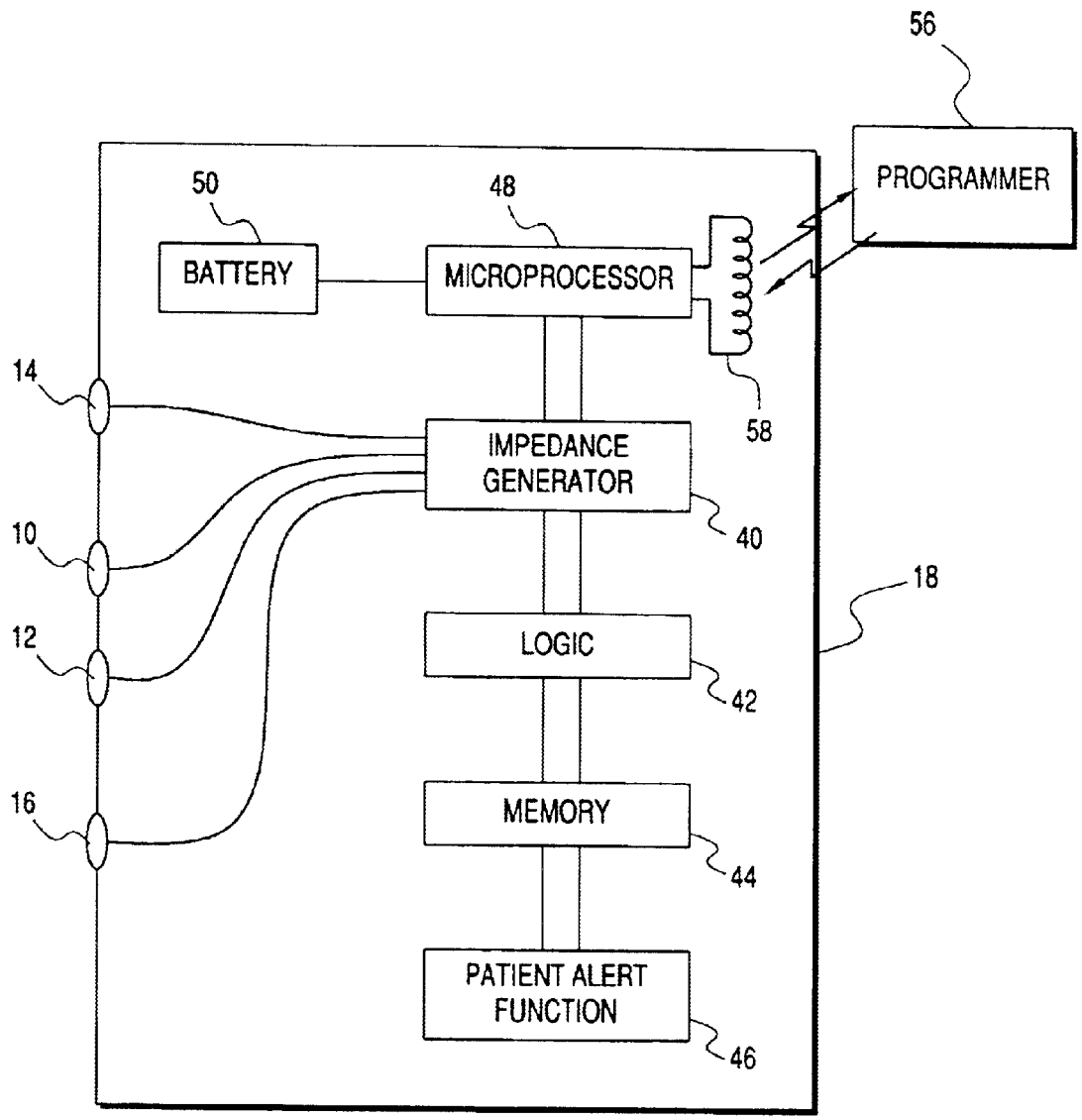
FIG. 3 is a block diagram of the internal circuitry of the device.

FIG. 3 illustrates the exemplary circuit module within device 18. An impedance signal generator 40 injects signal current into the body, preferably through "inner" electrodes 10 and 12. The current traverses the circuit path through the body portion of interest and has a return path through "outer" electrodes 14 and 16. Field lines 38 (FIG. 2) attributable to current flowing from the electrodes emanate from the concave side 26 of device 18, and, together with the electrode spacing, define the "viewing volume" of the device for the impedance sensing circuitry. Electrode spacing of at least four cm between the outer electrodes 14, 16 will allow a measurement to a depth of up to 10 cm of lung tissue in the anterior lateral lower left thorax. The field lines produced by current through the circuit path intersect the lung tissue 28 and are somewhat less influenced by the volume of the heart 30.

The circuit module within device 18 is powered by a preferably lithium-ion battery 50. Impedance generator 40 is controlled by microprocessor 48, as is logic 42 for analysis and memory 44 for data. Measured values of impedance are stored in memory 44, and used by microprocessor 48 to calculate long-term and short-term averages of the measured impedance values. A threshold detector 46 may be incorporated in device 18 as a patient alert function or alarm (e.g., by emitting an acoustic signal, vibrations, or low level pulses for local muscle contractions, recognizable by the patient) indicative of a need for immediate intervention when impedance associated with fluid level 64, for example, is detected. Such an alarm condition may also be signaled by telemetry from an antenna or coil 58 within the circuit module at the microprocessor, normally used to transmit the other impedance data, to a remote programmer 56 to monitor and log the progress of the disease and the therapeutic effect of treatment for review by the patient's physician.

The device is adapted to monitor impedance at a digital rate of 128 Hz, for partitioned analysis of contractile cardiac function, pulmonary ventilation function and long term pulmonary impedance, over an average of 72 hours or more. Signal processing allows deviation from basic impedance of the body region of interest, especially the lungs, to be detected as an early monitoring of a decrease in lung impedance, indicative of increasing congestion by fluid content in the lungs. The decrease in lung impedance associated with CHF occurs as the lungs fill with fluid, which is a considerably better electrical conductor than the normal lung tissue. Exemplary values of impedance for lung tissue are 400–1,000 ohms per centimeter ($\Omega$/cm), compared with 50 $\Omega$/cm for fluid.

Representative fluid levels accumulated in the lungs are illustrated in FIG. 2 at 60, 62 and 64. Level 60 represents the relative additional amount of fluid associated with normal lung function. Level 62 represents the relative amount of fluid present for a compromised lung function associated with CHF. And level 64 is the relative still additional amount of fluid associated with severely reduced lung function requiring immediate attention, indicative of advanced CHF.

The device 18 may be designed to provide a threshold or trigger level at an accumulation of fluid corresponding approximately to level 64. Algorithms are used to convert real time measurements into a diagnostic indication of congestion. The device may be operated continuously and the impedance data are then analyzed in kind. ECG data may be used additionally, detected at the outer electrodes 14 and 16 to improve the capability of the device to discern impedance changes in the heart.

Figure 4:
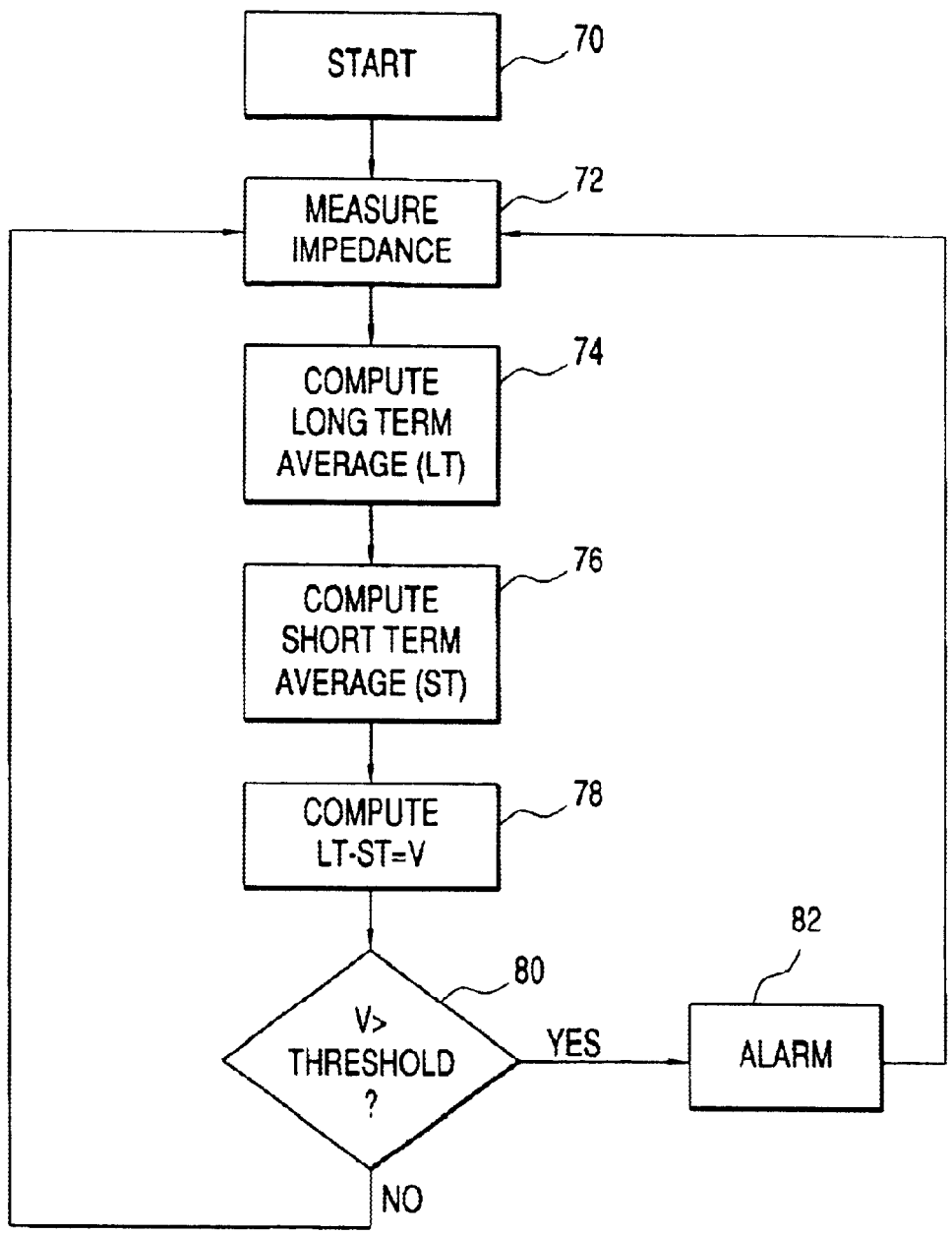
FIG. 4 is a flow chart illustrating the operation of the device.

FIG. 4 is a flow chart of an exemplary detection algorithm used by the device 18. On commencement counters are initialized and impedance generator 40 is turned on to inject signal current into the body via the inner pair of electrodes 10, 12 (start, 70). The impedance signal current is preferably a rectangular biphasic pulse wave at a rate of 128 Hz and a peak-to-peak amplitude of 1 milliampere (ma), or, alternatively, an alternating current in a range from 5 microamperes ($\mu$a) to 10 $\mu$a. The pulses may be injected with considerably higher energy content than the AC wave because of their very short duration (e.g., 15 $\mu$sec or less), with no risk of myocardial depolarization, and are capable of detecting cardiac changes as well as pulmonary changes.

Impedance is then calculated (72) from a measurement of the resulting voltage at the outer pair of electrodes 14, 16. Alternatively, a fixed voltage may be applied across the excitation (inner) electrodes and the resulting current measured at the measurement (outer) electrodes reflects the impedance. A long-term average of the impedance value is computed (74), covering a period ranging from days to weeks as a running average. A short-term average of the impedance value is also computed (76), covering a period from hours to days. The difference between the long-term (LT) and short-term (ST) averages is calculated (78) as a slope measurement (V) indicative of deterioration of the lung condition, to detect accelerating lung congestion. If the value V exceeds a predetermined threshold (slope) value (80), an alarm condition is indicated and the patient alert function (46, FIG. 3) is initiated. In either case (an alarm condition or not), another impedance measurement is performed (72) and the processing cycle is repeated.

In the description of FIG. 2, the detection of lung congestion requiring immediate attention was the result of a simple volume measurement. In practice, however, a slope measurement is preferred to determine when an alarm condition is occurring or has occurred, because the variability of impedance signals makes it more difficult to achieve accurate threshold detection by volume measurement.

Figure 5:
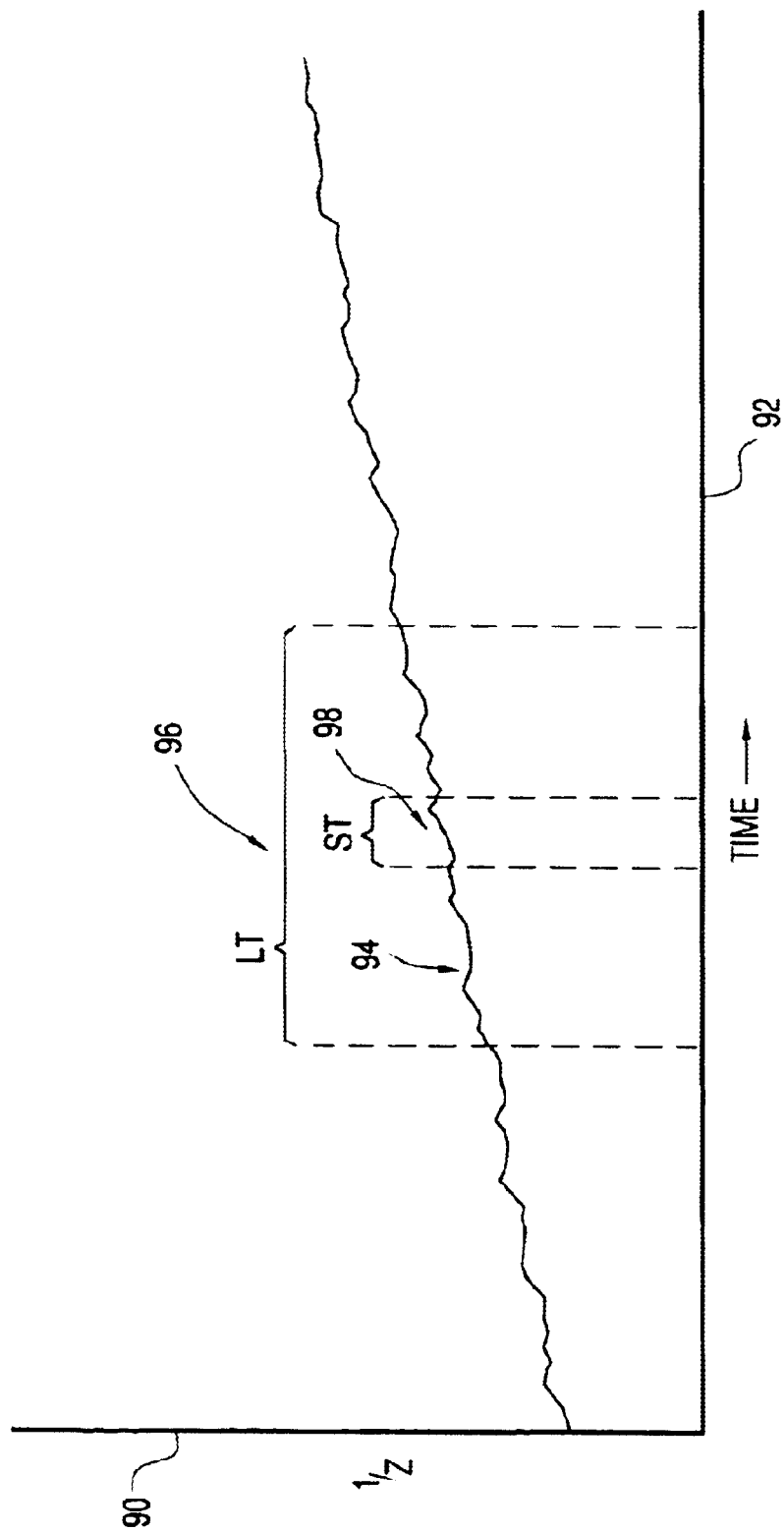
FIG. 5 is a graph of the device operation in terms of the reciprocal of impedance over time.

FIG. 5 is a graph of the device operation using the exemplary detection algorithm represented by the flow chart of FIG. 4. The vertical axis 90 is conductance, the reciprocal of impedance (1/Z). Therefore, the greater the lung congestion (i.e., the larger the fluid volume in the patient's lungs), the higher the value of the term 1/Z. The horizontal axis 92 represents time. The long-term average of the impedance measurement has a characteristic value that filters out the short-term variations of the measurement. In the Figure, the LT value 96 of curve or slope 94 exhibits a more gradual slope than the ST value 98. The difference between the two is used to determine whether an alarm condition is occurring (LT−ST=V≧threshold).

In addition to the baseline impedance, impedance measurements at the frequency of 128 Hz can detect impedance changes with every pumping cycle, to provide indirect information on stroke volume, heart rate, and cardiac output calculated therefrom. Additionally, by adequate low pass filtering, the indirect tidal volume of ventilation can be separated out, as well as respiratory rate. Typically, ventilation is in a range from 0.2 Hz to 0.8 Hz, while cardiac events are in a range from 1 Hz to 3 Hz. Both subsignals, cardiac and ventilation, are used in addition to determine congestive heart failure indicated by increase in stroke volume, decrease in tidal volume, increase in heart rate, and increase in ventilation rate.

A power saving can be achieved in the device by limiting the impedance measurement to fixed periods separated by intervals of no measurement, or even sporadic measurements, rather than performing continuous impedance measurements.

The impedance measurement electrodes may be used to monitor the patient's ECG, as well as to obtain the raw data necessary for calculating absolute impedance and long and short-term averages of impedance. Also, the cardiac- and ventilation-derived impedance phenomena may be correlated to the ECG for better evaluation.

It is important to consider the factor of where the measurements are taken as well as the manner of obtaining the measurements. For example, the spacing between the measurement electrodes 14, 16 determines the volume and area of measurement. By spacing these electrodes at least 4 cm apart, the depth of measurement is increased beyond only the tissue in the immediate vicinity of the electrode, to the tissue for which specific impedance and impedance changes are sought to be measured, typically to a depth of up to 10 cm of lung tissue. Also, performing the measurements on the patient's left side rather than the right side, and particularly on the anterior lateral lower left thorax, enables early detection of changes in left ventricular parameters and congestion in the lung circulatory system, rather than limiting the measurement to tissue and liver impedance which is primarily a function of congestion of the right heart. Additionally, at this preferred location for conducting the measurements, the cardiac phenomena and stroke volume dependent impedance changes are more easily detected than on the right side or the upper left thorax where impedance changes primarily follow blood circulation.

Although a presently contemplated best mode, preferred embodiment and method of practicing the invention have been described in this specification, it will be apparent to those skilled in the art from a consideration of the foregoing description, that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. An implantable device-implemented method of detecting and monitoring congestive heart failure in a patient, which comprises the steps of:
   measuring local impedance of a portion of the patient's body generally occupied by the lungs solely through surface mounted electrodes on the device with the device implanted subcutaneously in the patient's body at the locality where the impedance measurements are to be performed, and
   determining when the impedance measurements are indicative of a condition of congestive heart failure other than from the existence of a state of edema of the patient.

2. The device-implemented method of claim 1, including performing said measurements continuously.

3. The device-implemented method of claim 1, including performing said measurements periodically to reduce power consumption of the device.

4. The device-implemented method of claim 1, including performing said measurements from sporadically to reduce power consumption of the device.

5. The device-implemented method of claim 1, including performing said impedance measurements in part by injecting electrical current into said body portion.

6. The device-implemented method of claim 5, including injecting said electrical current into said body portion through at least one of said surface mounted electrodes of the device.

7. The device-implemented method of claim 5, including performing said impedance measurements in part by monitoring said injected electrical current returning via at least one other of said surface mounted electrodes of the device positioned in said body portion.

8. The device-implemented method of claim 5, including injecting said electrical current in the form of a biphasic pulse wave.

9. The device-implemented method of claim 1, including averaging said impedance measurements over long term and short term periods, and calculating the difference between the long term and short term averages representative of the slope of the reciprocal of impedance over time.

10. The device-implemented method of claim 9, including comparing said slope of the reciprocal of impedance over time against said predetermined threshold value, and triggering a patient alert signal when said slope exceeds the predetermined threshold value.

11. The device-implemented method of claim 1, including using said surface mounted electrodes of the device additionally to monitor the patient's EGG.

12. The device-implemented method of claim 11, wherein the device is implanted subcutaneously at the lower left side of the thoracic cage.

13. The device-implemented method of claim 1, including performing said impedance measurements with the device implanted on the lower left side of the thoracic cage.

14. The device-implemented method of claim 1 wherein said body portion further encompasses the patient's heart, including performing said impedance measurements by means of a signal injected into said body portion from the device and retrieved as a signal subdivided into a cardiovascular portion, a ventilation portion, and a total impedance portion.

15. The device-implemented method of claim 1, including determining when the impedance measurements exceed a predetermined threshold value indicative of a need for immediate attention to a condition of congestive heart failure.

16. A body-implantable device to detect and monitor congestive heart failure in a patient, comprising a circuit module having surface mounted electrodes of the device arranged, when the device is implanted subcutaneously, for exposing said electrodes to tissue in a portion of the patient's body generally occupied by the lungs, said circuit module including circuitry that measures impedance of said body portion through said surface mounted electrodes and determines when the impedance measurements are indicative of a condition of congestive heart failure wherein the determination of congestive heart failure is based on factors other than the existence of edema of the patient.

17. The device of claim 16, wherein said circuit module includes an excitation pair and a measurement pair of said surface-mounted electrodes, and a current generator for injecting current into said body portion through said excitation pair.

18. The device of claim 17, wherein said circuit module includes detection apparatus for monitoring at said measurement pair of said surface mounted electrodes an electrical parameter attributable to said injected current, reflecting impedance changes.

19. The device of claim 18, wherein the electrodes of said measurement pair of surface mounted electrodes are spaced apart by at least 4 cm.

20. The device of claim 16, wherein said circuit module performs said impedance measurements according to an algorithm in which the measured impedance is averaged over long term and short term periods.

21. The device of claim 16, wherein said circuit module is contained within a case having a curvilinear shape adapted to conform to the shape of a portion of the patient's body at the implant site.

22. The device of claim 21, wherein said curvilinear shape of the case conforms to the curvature of the patient's rib cage in the vicinity of the implant site.

23. A body-implantable medical device for monitoring the condition of a patient at risk for congestive heart failure, comprising circuitry, including plural surface electrodes on the device, that measures impedance between a measurement pair of said electrodes from a predetermined electrical parameter injected in a circuit path between an excitation pair of said electrodes, such that when said device is implanted at a site where said circuit path includes the patient's cardiovascular and pulmonary system through said plural surface electrodes only, said impedance measurements indicate a state of lung congestion of the patient.

24. The device of claim 23, wherein said device is designed to be implanted at a site on the left lower hemithorax of the patient's body.

25. An implantable device-implemented method of detecting and monitoring congestive heart failure in a patient, which comprises the steps of:

performing impedance-derived ventilation measurements of a portion of the patient's body generally occupied by the lungs through surface mounted electrodes on the device with the device implanted subcutaneously in the patient's body at the locality where the impedance measurements are to be performed, and determining when the impedance-derived ventilation measurements are indicative of a condition of congestive heart failure based on factors other than the existence of edema.

26. A body-implantable device to detect and monitor congestive heart failure in a patient, comprising a circuit module having surface electrodes of the device arranged, when the device is implanted, for exposing said electrodes to tissue in a portion of the patient's body generally occupied by the lungs, said circuit module including circuitry that performs impedance-derived ventilation measurements of said body portion solely through said surface electrodes of the device and determines directly from said impedance-derived ventilation measurements whether the patient is exhibiting a condition of congestive heart failure.

27. A body-implantable medical device for monitoring the condition of a patient at risk for congestive heart failure, comprising circuitry, including plural surface electrodes on the devices for making impedance-derived ventilation measurements between a measurement set of said electrodes from a predetermined electrical parameter injected in a circuit path between an excitation set of said electrodes and for determining, when said device is implanted at a site where said circuit path includes the patient's cardiovascular and pulmonary system through said plural surface electrodes, whether said impedance-derived ventilation measurements are indicative of a state of congestive heart failure of the patient.

28. The body-implantable device of claim 27, wherein said circuitry also serves to monitor the patient's ECG through said measurement set of the electrodes.

29. A body-implantable device to detect and monitor congestive heart failure in a patient, comprising a circuit module having surface-mounted electrodes of the device arranged, when the device is implanted, for positioning outside the thoracic cage and for exposing said electrodes to tissue in a portion of the patient's body generally occupied by the lungs, said circuit module including circuitry that measures impedance of said body portion exclusively through said electrodes and detects from the impedance measurements of a condition of congestive heart failure other than solely from the existence of a state of edema of the patient.

30. The body-implantable device of claim 29, wherein said circuit module performs said impedance measurements according to an algorithm in which the measured impedance is analyzed with respect to ventilation and baseline impedance changes.

31. The body implantable device of claim 29, wherein said circuit module is contained within a case having a curvilinear shape that conforms to the shape of a portion of the patient's body at the implant site.

32. The body-implantable device of claim 31, wherein said curvilinear shape of the case conforms to the curvature of the patient's rib cage in the vicinity of the implant site, and said electrodes are located on a side of the case facing the vertical center of the body.

* * * * *